United States Patent
Kittrell et al.

(10) Patent No.: US 11,708,343 B2
(45) Date of Patent: Jul. 25, 2023

(54) METHOD AND INTEGRATED PROCESS FOR THE CARBOXYLATION OF FURAN DERIVED CARBOXYLIC ACIDS TO 2,5-FURANDICARBOXYLIC ACID

(71) Applicant: KSE, Inc., Sunderland, MA (US)

(72) Inventors: James R. Kittrell, Belchertown, MA (US); Carl R. Dupre, Amherst, MA (US); Keith D. Kittrell, Amherst, MA (US); Leonard T. McDonald, Greenfield, MA (US); Jeffrey A. Kittrell, The Woodlands, TX (US)

(73) Assignee: KSE, Inc., Sunderland, MA (US)

( * ) Notice: Subject to any disclaimer, the term of this patent is extended or adjusted under 35 U.S.C. 154(b) by 0 days.

(21) Appl. No.: 17/377,851

(22) Filed: Jul. 16, 2021

(65) Prior Publication Data

US 2023/0020051 A1    Jan. 19, 2023

(51) Int. Cl.
*C07D 307/68*    (2006.01)

(52) U.S. Cl.
CPC .................................. *C07D 307/68* (2013.01)

(58) Field of Classification Search
CPC .................................................... C07D 307/68
USPC .......................................................... 549/485
See application file for complete search history.

(56) References Cited

U.S. PATENT DOCUMENTS

| | | | |
|---|---|---|---|
| 3,567,646 A | 3/1971 | Gray | |
| 8,338,626 B2 | 12/2012 | Gruter et al. | |
| 8,519,167 B2 | 8/2013 | Munoz De Diego et al. | |
| 8,558,018 B2 | 10/2013 | Sanborn | |
| 9,284,290 B2 | 3/2016 | Van Haveren et al. | |
| 10,160,740 B2 | 12/2018 | Kanan et al. | |
| 10,710,971 B2 | 7/2020 | Kanan et al. | |
| 10,844,031 B2 | 11/2020 | Sadow et al. | |
| 2020/0181782 A1 | 6/2020 | Redko et al. | |

FOREIGN PATENT DOCUMENTS

| | | | | |
|---|---|---|---|---|
| CN | 109678823 A | | 4/2019 | |
| CN | 110437186 A | * | 11/2019 | ........... C07D 307/48 |
| CN | 111138392 A | | 5/2020 | |
| CN | 111153877 A | | 5/2020 | |
| KR | 102117340 B1 | | 6/2020 | |
| WO | 2019214576 A1 | | 11/2019 | |
| WO | 2021/158890 A1 | | 8/2021 | |

OTHER PUBLICATIONS

Dick et al , A scalable carboxylation route to furan-2,5-dicarboxylic acid, Green Chem.,2017,19, 2966-2972 (Year: 2017).*

(Continued)

*Primary Examiner* — Taylor V Oh (74) *Attorney, Agent, or Firm* — Bachman & LaPointe, P.C.

(57) ABSTRACT

A process for carboxylation of a furoate slurry to produce FDCA, especially 2,5-FDCA, includes the steps of: feeding a slurry containing a suspension fluid, furoate, a surfactant and an alkali metal carbonate to a carboxylation reactor; and feeding a flow of $CO_2$ to the carboxylation reactor at flow conditions sufficient to suspend the slurry in the reactor and react the furoate with CO2 to form 2,5-FDCA. A fully integrated process is also disclosed.

17 Claims, 6 Drawing Sheets

(56) References Cited

OTHER PUBLICATIONS

Wilson, 2-Furancarboxylic Acid and 2-Furylcarbinol, Organic Syntheses, Coll. vol. 1, p. 276 (1941); vol. 6, p. 44-47, 1926) (Year: 1926).*

Wikipedia, Surfactant, Feb. 2020, p. 1-11. (Year: 2020).*

Nakajima et al., "The Recent Developments in Biobased Polymers toward General and Engineering Applications: Polymers That Are Upgraded from Biodegradable Polymers, Analogous to Petroleum-Derived Polymers, and Newly Developed", Polymers 2017, vol. 9, No. 523, pp. 1-26.

Sax, L., "Polyethylene Terephthalate May Yield Endocrine Disruptors", Environmental Health Perspectives, Apr. 2010, vol. 118 No. 4, pp. 445-448.

Luciani-Torres et al., Exposure to the Polyester PET Precursor—Terephthalic Acid Induces and Perpetuates DNA Damage-Harboring Non-Malignant Human Breast Cells. Carcinogenesis 2014, vol. 36, No. 1, pp. 168-176.

Pflug, I.J., et al., "Fundamentals of Carbon Dioxide Absorption as They Apply to Controlled Atmosphere Storages", Quarterly Bulletin of the Michigan Agricultural Experimental Station, Aug. 1957, vol. 40, No. 1, pp. 131-138.

Aanindeeta Banerjee et al: "Carbon dioxide utilization via carbonate-promoted C–H carboxylation", Nature, vol. 531, No. 7593, Mar. 1, 2016, pp. 215-219, XP055543058, London ISSN: 0028-0836, DOI: 10.1038/nature17185.

Partenheimer W et al: "Synthesis of 2,5-diformylfuran and furan-2,5-dicarboxylic acid by catalytic air oxidation of 5-hydroxymethylfurfural. Unexpectedly selective aerobic oxidation of benzyl alcohol to benzaldehyde with metal/bromide catalysts", Advanced Synthesis and Catalysis,, vol. 343, No. 1, Jan. 1, 2001, pp. 102-111, XP002584717,ISSN: 1615-4150.

International Search Report and Written Opinion dated Nov. 4, 2022 for corresponding application PCT/US2022/037237.

* cited by examiner

2,5 - FDCA

FIG. 6

2,4 - FDCA

FIG. 7

3,4 - FDCA

FIG. 8

2,3 - FDCA

METHOD AND INTEGRATED PROCESS FOR THE CARBOXYLATION OF FURAN DERIVED CARBOXYLIC ACIDS TO 2,5-FURANDICARBOXYLIC ACID

GOVERNMENT RIGHTS

This invention was made with government support under DOE Award #DE-SC0017219 awarded by the Department of Energy. The government has certain rights in the invention.

BACKGROUND

This disclosure relates to the preparation of furandicarboxylic acid (FDCA), especially 2,5-FDCA, from a furan derivatized carboxylate salt produced from sugar bearing sources such as C5 and C6 sugar bearing sources, especially C5 sugar bearing sources.

The production of 2,5-furandicarboxylic acid has gained significant interest over the last decade, as polyesters derived from FDCA have demonstrated superior mechanical strength and gas permeability properties when compared with polyesters derived from purified terephthalic acid (PTA). The food and beverage industry, in particular, have shown interest in these properties for improved beverage transport and long-term storage. However, such product derived from the esters of terephthalic acid have been cited as a possible endocrine disruptor due to leaching of the polyesters into food stuffs.

Current methods in the art for the industrial production of FDCA include synthesis routes that use the oxidation of 5-hydroxymethylfurfural (HMF) or derivatives such as 5-alkoxymethylfurfural ethers. Such compounds are synthesized from fructose and glucose C6 sugars. These sugars are converted to 5-alkoxymethylfurfural ethers through a complicated series of reactions that may require the use of zeolite catalysts and/or strong acids and solvents to produce the desired products to be used as feedstock for FDCA synthesis, as detailed in U.S. Pat. No. 8,338,626. The furan compounds can then be oxidized using mixtures of Co/Mn/Br with air or molecular oxygen as an oxidizing source, as described in U.S. Pat. No. 8,519,167.

U.S. Pat. No. 9,284,290 provides a method in which FDCA is produced from potassium furoate. While this method provides a possible means to produce FDCA, the use of platinum metal group catalysts, and/or toxic co-catalysts make this a less desirable method. Moreover, the disproportionation reaction may limit the theoretical yields to about 50% FDCA.

Another method known in the art, U.S. Pat. No. 10,160,740, uses carbonate ($CO_3^-$) promoted carboxylation reactions using mixed alkali metal furoate salts as a feedstock. Several methods of production were reported, such as continuous flow of $CO_2$ in a fixed bed flow reactor, and dispersion of $CO_2$ through the constant rotation of the mass in a rotary evaporator apparatus. These methods reported reaction times around 48 hours. Furthermore, the prior art uses reaction schemes that are ill suited for continuous processing.

The present disclosure addresses these issues.

SUMMARY

The processes of the present disclosure can provide rapid and continuous production of FDCA from furan derived carboxylic acids. The reaction pathway disclosed herein provides a synthesis route using C5 sugars for the production of FDCA, establishing a process that utilizes $CO_2$, a harmful greenhouse gas, and the furan carboxylic acids.

The invention claimed in this application can combine reactive distillation to convert C5 sugars derived from any lignocellulose source to a furan derivative, oxidation of the furan derivative into alkali metal furoate salt for direct carboxylation, ultimately to FDCA, including regeneration of the carbonate promoter. Lignocellulose source materials are widely available, for example from wet waste streams from hardwood pulp and paper mills. Use of a dilute furfural stream and controlling the rate of addition during oxidation increases yield of the furoate salt. A suspension reactor may be used for the carboxylation step, overcoming the limitations of prior art described using a molten salt reaction medium. The suspension reactor distributes $CO_2$ to dispersed particles of furoic acid salts. This is due to the entraining of large volumes of $CO_2$ within the suspension fluid. The suspension fluid prevents the agglomeration of the furoic acid particles during the course of the reaction. The suspension medium, in conjunction with surfactants, facilitates the particles to remain discrete and free flowing. FDCA synthesis from selective intermediates coupled with the use of a suspension reaction as a means to facilitate a carboxylation reaction has not been established in either scientific literature or the prior art. The process of the present disclosure produces FDCA with a selectivity toward 2,5-FDCA but also including other isomers of FDCA including 2,3-FDCA, 2,4-FDCA and 3,4-FDCA which will collectively be referred to herein as FDCA.

In a non-limiting embodiment, the produced FDCA comprises a majority fraction, measured by weight, of 2,5-FDCA.

In one non-limiting embodiment, a process for carboxylation of a furoate slurry to produce FDCA is disclosed, which comprises the steps of: feeding a slurry containing a suspension fluid, furoate, a surfactant and an alkali metal carbonate to a carboxylation reactor; and feeding a flow of $CO_2$ to the carboxylation reactor at flow conditions sufficient to suspend the slurry in the reactor and react the furoate with $CO_2$ to form FDCA.

In another non-limiting embodiment, the suspension fluid demonstrates characteristics sufficient to maintain a suspension of reactant particles, readily absorbs C02, is thermally stable and non-flammable.

In still another non-limiting embodiment, the suspension fluid is selected from the group consisting of paraffinic solution, fatty acid solution, and combinations thereof.

In a further non-limiting embodiment, the suspension fluid is present in the slurry at a mass ratio of suspension fluid to solids in a slurry of between 7:1 and 1:1.

In a still further non-limiting embodiment, a temperature in the reactor is between 10 and 500° C.

In another non-limiting embodiment, pressure in the reactor is between 3 and 15 bar.

In still another non-limiting embodiment, the alkali metal carbonate is a promoter and can contain an alkali metal that is the same or different from the surfactant and the furoate.

In a further non-limiting embodiment, the slurry contains surfactant and furoate at a furoate to surfactant mass ratio of between 4:1 and 628:1.

In a still further non-limiting embodiment, the slurry and the $CO_2$ in the reactor form particles of mixture comprising a droplet of suspension fluid containing a reactant bead and at least one $CO_2$ bubble.

In another non-limiting embodiment, a finished reaction slurry is removed from the reactor, and further comprising feeding the finished reaction slurry to a solid/fluid separator to produce separated solids, feeding the separated solids to a dissolver/mixer unit to dissolve the solids to produce a dissolved product, and feeding the dissolved product to a precipitation reactor to precipitate and separate the desired 2,5 FDCA.

In still another non-limiting embodiment, the slurry is prepared by mixing a dried furoate with the surfactant and the alkali metal carbonate with the suspension fluid in a mixer.

In a further non-limiting embodiment, the alkali metal carbonate is regenerated from an alkali metal chloride by ion exchange into an alkali metal hydroxide and then gas absorption of the alkali metal hydroxide with $CO_2$ to produce the alkali metal carbonate.

In a still further non-limiting embodiment, the furoate is prepared by oxidizing furfural in the presence of an alkali metal hydroxide.

In another non-limiting embodiment, the furfural is prepared by reactive distillation of a C5 sugar source in the presence of an acid catalyst and polymerization inhibitor.

In a non-limiting embodiment, an integrated process for preparation of FDCA, especially 2,5-FDCA, comprises the steps of: furfural is prepared by catalytic and reactive distillation of a C5 sugar source, feeding furfural and alkali metal hydroxide to an oxidation reactor to produce furoate; feeding the furoate to a drier to produce a dried furoate; feeding the dried furoate, an alkali metal carbonate, a surfactant and a suspension fluid to a mixer to form a slurry; feeding the slurry to a carboxylation reactor for contacting with a stream of $CO_2$ so as to produce a finished product containing FDCA; feeding the finished product to a solid/fluid separator to generate a separated fluid and a solid finished product; feeding the solid finished product to a dissolver/mixer to form a dissolved finished product, and feeding the dissolved finished product to a precipitation reactor in the presence of an acid to obtain a final FDCA product and an alkali chloride; recycling the separated fluid from the solid/fluid separator to the mixer as recycle suspension fluid; feeding the alkali chloride from the precipitation reactor to an ion exchange reactor to produce a recycled alkali metal hydroxide as recycle feed to the oxidation reactor, and feeding at least a portion of the recycled alkali metal hydroxide to contact a $CO_2$ stream in a gas absorber to produce a regenerated alkali metal carbonate; and recycling the regenerated alkali metal carbonate to the mixer.

BRIEF DESCRIPTION OF THE DRAWINGS

A detailed description follows, with reference to the accompanying drawings, wherein.

DETAILED DESCRIPTION

The present disclosure relates to a process for production of furandicarboxylic acid (FDCA), especially 2,5-FDCA and its isomers 2,4-FDCA, 3,4 FDCA, and 2,3-FDCA, collectively referred to herein as FDCA.

Figure 1:
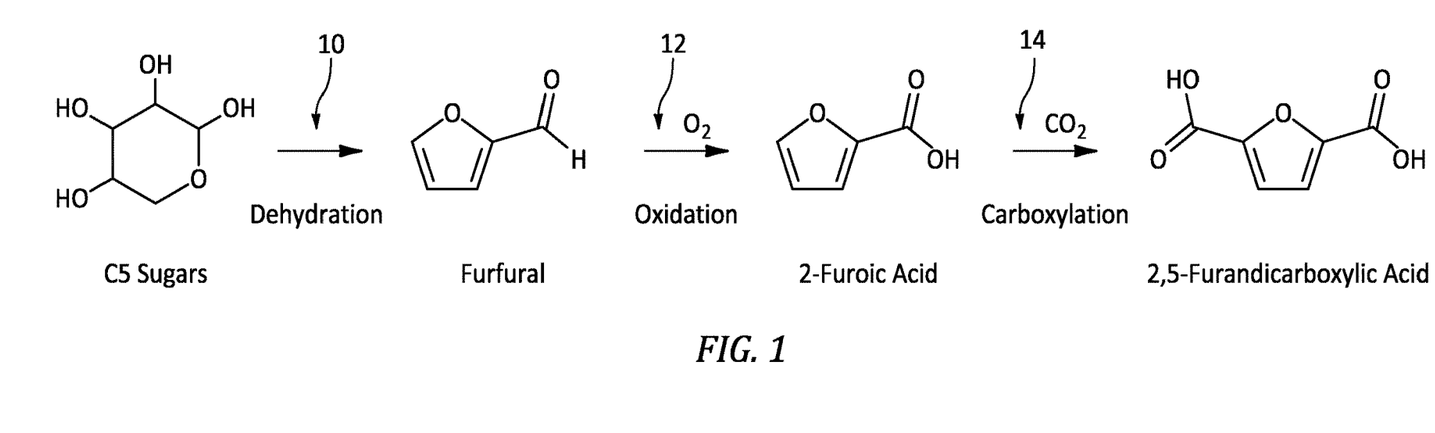
FIG. 1 schematically illustrates the reaction sequence from starting material to FDCA.

FIG. 1 shows the reaction route to produce FDCA from lignocellulose derived sugars. In the disclosed process, there is a natural selectivity to 2,5-FDCA, thus the product will comprise a majority fraction by weight of 2,5-FDCA. It should be appreciated that with modification of parameters of the process steps, the process could be adapted to produce other isomers at different amounts. All such modifications are considered to be within the broad scope of this disclosure.

In the figure, in a first step 10, catalytic dehydration of C5 sugars is conducted to produce 2-furan aldehyde (furfural). In the next step 12, furfural is subjected to a catalytic oxidation, in one configuration using mixed metal catalyst and an oxygen bearing feed stream, to produce 2-furan carboxylic acid (2-furoic acid), and subsequently alkali metal furoate, with high selectivity. This is the desired feedstock to the carboxylation step (step 14), where the furoate is carboxylated using a continuous $CO_2$ feed stream to produce the desired product 2,5-furandicarboxylic acid (2,5 FDCA).

Figure 2:
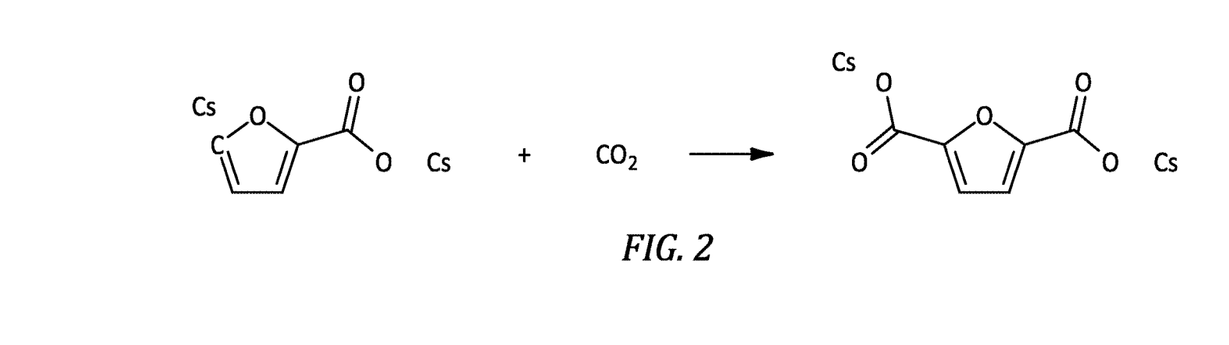
FIG. 2 schematically illustrates carboxylation of 2-furoate by direct addition of $CO_2$ where the alkali metal ion is represented by cesium for example.

FIG. 2 illustrates the carboxylation step for carboxylation of cesium furoate for example to cesium FDCA salt. This shows nucleophilic addition of a carboxylate acid functional group to the furan ring, and the structure is stabilized through the ionic bond associated with the alkali metal ion, here cesium. This is representative of the reaction carried out through the direct addition of $CO_2$, and will be further described below.

Figure 3:
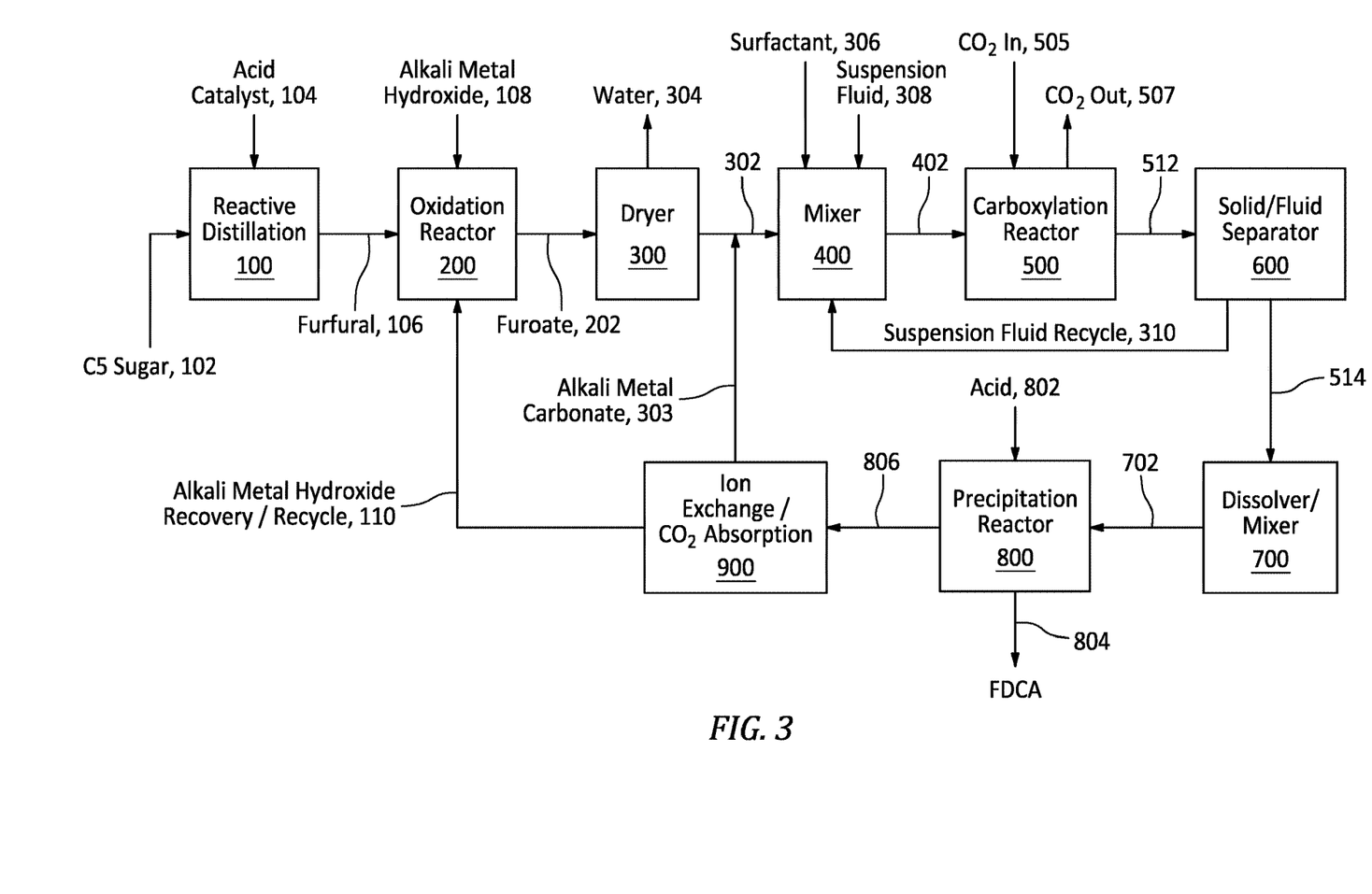
FIG. 3 illustrates a fully integrated process according to the present disclosure.

FIG. 3 shows an integrated process for producing FDCA according to this disclosure. In this integrated process, the sequence of reactions illustrated in FIG. 1 can be conducted. Two inlet streams provide the necessary feedstock for the process with a clearly defined route to the final product formation. Recycle streams are included as may be needed or desired within the process. However the process can be modified and adjusted for different additional concerns as may be apparent to a person having skill in the art.

In FIG. 3, block 100 represents a catalytic reactive distillation step which converts C5 sugars contained in a hemicellulose feedstock source into 2-furan aldehyde (furfural). This corresponds to step 10 in FIG. 1. Feeds to the reactor at block 100 include a C5 sugar source feedstock 102 and an acid catalyst 104. The C5 sugar source feedstock can be derived from any lignocellulose source, such as, for example, woody substrates such as hardwood, softwood, agri-residues, dedicated energy crops, or municipal solid wastes. These materials can be available in large supply from various sources with one example being a wet waste stream from hardwood pulp and paper plants. Further, other sugar source feedstock can be used including, but not limited to, C6 sugar sources. Within this context, C5 sugar source feedstock has been found to be particularly well suited to the disclosed process.

The acid catalyst 104 can be mineral acids such as sulfuric or hydrochloric acid and/or solid acids such as silico-aluminates (zeolites, alumina, etc.).

Lignocellulose, such as hemicellulose for example, contains xylan/xylose compounds that can be converted to the furfural intermediate product via hydrolysis of xylan to xylose, followed by dehydration to furfural in the presence of the acid catalyst. A representation of this process is shown in FIG. 4a and a suitable reactor is shown in FIG. 4b.

Figure 4A:
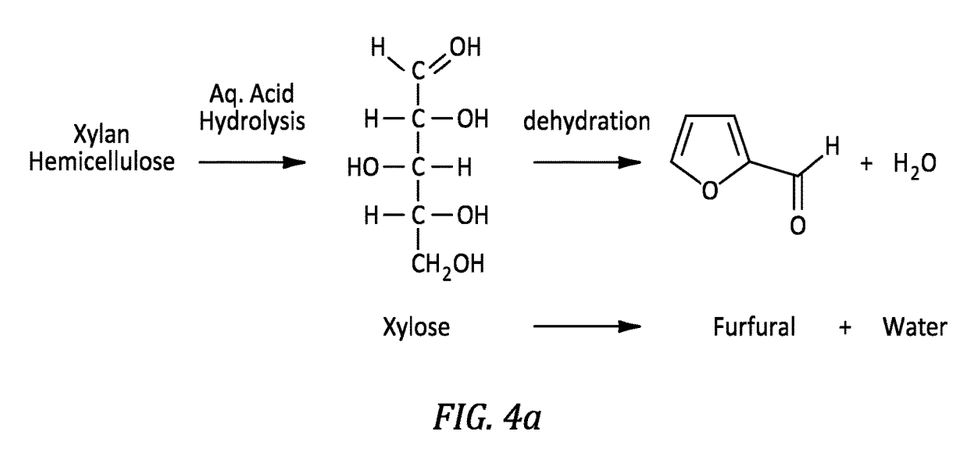
FIGS. 4*a* and 4*b* schematically illustrate hydrolysis of xylan to xylose followed by dehydration to furfural in the presence of an acid catalyst as well as a reactive distillation column for carrying out this step.
Figure 4B:
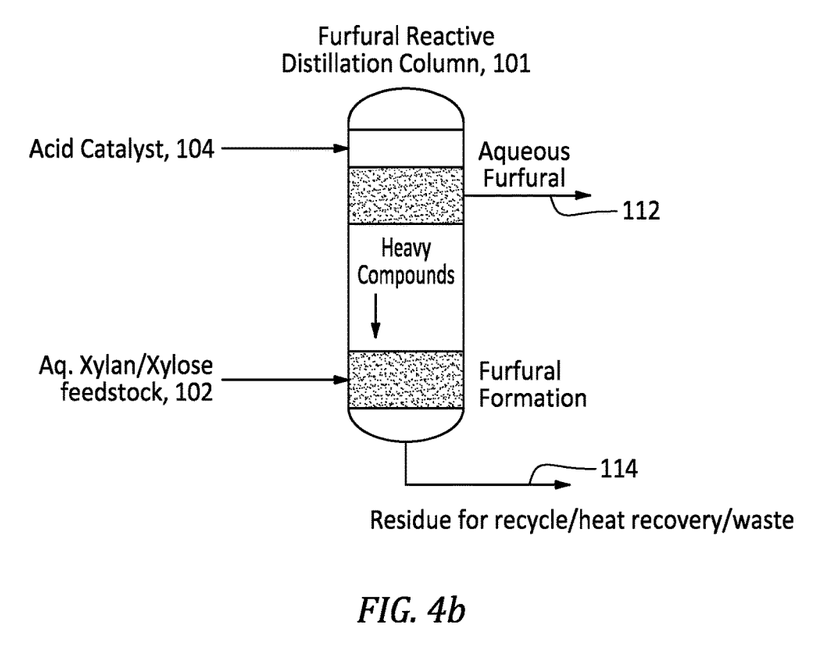

In FIG. 4a, the reaction to obtain furfural from xylan hemicellulose is shown. In FIG. 4b, a reactive distillation column 101 is shown with inlet 102 for aqueous xylan/xylose feedstock and inlet for acid catalyst 104. Furfural is formed in the reaction zone and rapidly separated overhead via distillation as an aqueous furfural stream 112. Heavy components settle within column 101 and a residue is removed through outlet 114. This residue can be further treated for recycle, heat recovery or as a waste product. Further aspects of the reactive distillation are set forth below.

Pyridine, quinoline or other polymerization inhibitors, can be introduced in this step to mitigate polymerization with pentosan intermediates thereby preserving high furfural selectivity.

Produced furfural can be rapidly separated from the liquid reaction medium by removal from an internal tray that can advantageously be incorporated in the reaction column 101. Reactive distillation utilizes volatile components of the reaction mixture itself, primarily water. No additional water, in the form of steam, needs to be added.

Heavy components from the distillation, such as polysaccharides of xylose, homogeneous catalyst, lignin, hemicellulose components other than xylan and the like, can remain in the reboiler of the distillation column. These heavy components can be reclaimed for fuel value or recycled back to the dehydration reactor for further conversion of xylan compounds. Distillation also produces a dilute furfural stream 106 that can be directed to an oxidation reactor for the next steps in the process.

The reactive distillation conducted in step 100 can be conducted at process conditions including a temperature in the range of 100-125° C. and a pressure in the range of 1-10 bar.

Referring back to FIG. 3, block 200 represents an oxidation reactor that oxidizes furfural such as furfural from furfural stream 106, to furoic acid in the presence of an alkali metal hydroxide 108 or recycle alkali metal hydroxide from stream 110. Recycling of alkali metal hydroxide is further discussed below. Oxidation can be conducted at process conditions including a temperature in the range of 45-200° C. and a pressure in the range of 1-10 bar in the presence of transition metal catalysts.

The main product of the oxidation step or block 200 is a stream 202 of alkali metal furoate, which is the feedstock for the carboxylation reaction. The product stream 202 can be directed to a continuous drying apparatus, block 300, via stream 202. The continuous drying apparatus can be any such device that is common to the industry. Drying can be conducted at a temperature of between 200 and 300° C., and a pressure of 1 bar, to generate a stream 302 of dried furoate and water 304. The water 304 removed during this process can be used as waste steam or recycled to block 200 or elsewhere as the process dictates and/or as or where there is need for water.

The dried furoate material in stream 302 can then be directed to a mixing vessel represented at block 400. The mixing vessel 400 can be used to blend the dried furoate compound with an alkali metal carbonate which can come via stream 303 from a recycle loop, or from any other suitable source. In addition, a surfactant can be added to mixer 400 via stream 306, and a suspension fluid can be added via stream 308 and/or a suspension fluid recycle stream 310.

The suspension fluid in mixer 400 should be able to absorb sufficient quantities of $CO_2$ such that the suspension fluid becomes saturated with $CO_2$ and maintains a suspension of particles in the reactants in mixer 400. In addition, the suspension fluid should also be thermally stable at expected temperatures in the reactor, and non-flammable. The ability of a suspension fluid to absorb $CO_2$ is a function of the fluid itself as well as conditions within the reactor. Nevertheless, particularly suitable suspension fluids include but are not limited to paraffinic solutions, fatty acid solutions, and combinations thereof.

Suspension fluid is preferably utilized in the slurry in the reactor at a mass ratio of suspension fluid to solids in the slurry of between 7:1 and 1:1. Further, the slurry preferably contains surfactant and furoate at a furoate to surfactant mass ratio of between 4:1 and 628:1. The product of mixer 400 is a furoate slurry shown at stream 402.

The furoate slurry in stream 402 can next be transferred into a carboxylation reactor, shown at block 500 as a stirred-tank reactor, and can be passed through a heating zone. The slurry may be transferred to reactor 500 through any slurry handling method common to industry. The slurry contains a mixture of furoate/carbonate/surfactant which is entered into reactor 500 and contacted with $CO_2$. In one non-limiting embodiment, the $CO_2$ can be pumped in a co-current flow with stream 402. Alternatively, flow can be counter-current and/or a combination of these flows.

Figure 5:
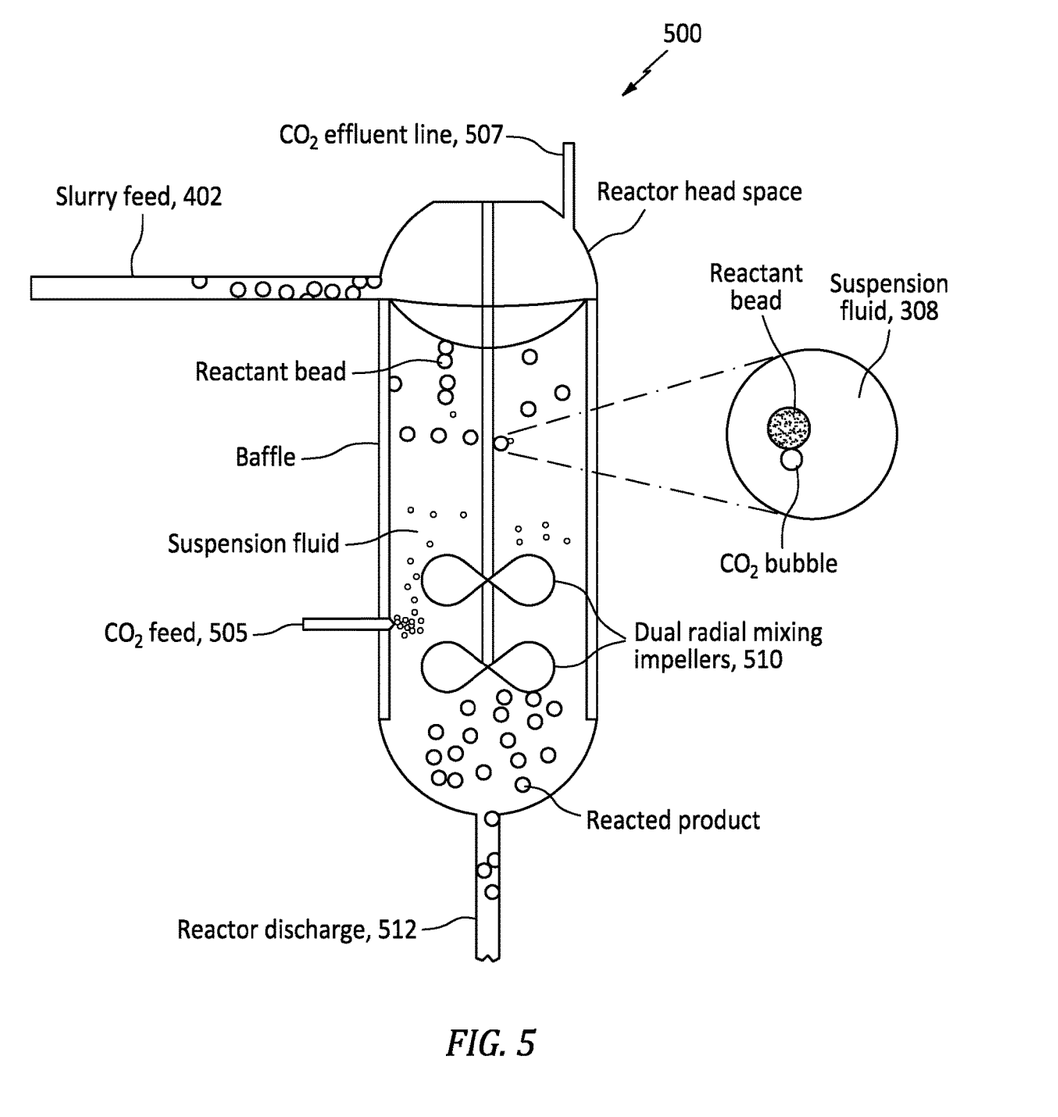
FIG. 5 illustrates a non-limiting configuration of a reactor for carrying out the carboxylation reaction described herein.
Figure 6:
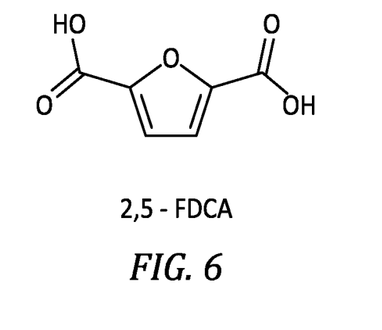
FIGS. 6-9 illustrate 2,5-FDCA (FIG. 6) and its isomers 2,4-FDCA (FIG. 7) 3,4 FDCA (FIG. 8), and 2,3 FDCA (FIG. 9) which can be produced following the process of this disclosure.

Reactor 500 is operated to allow for a suspension of particles to be maintained during the course of the carboxylation reaction. FIG. 5 schematically illustrates one non-limiting configuration of reactor 500. FIG. 5 also clearly exemplifies the process carried out in reactor 500. A continuous slurry feed can be introduced via an inlet line 402 which can preferably be communicated into the reactor at or near the top of the reactor. A continuous $CO_2$ stream is established in the reactor from a side inlet stream, for example $CO_2$ feed inlet 505. An effluent outlet 507 can be located at or near the top of reactor 500. Reactor 500 is also configured and operated to provide an isothermal profile in the reactor. A continuous draw in the bottom of the reactor, shown at reactor discharge 512, allows for removal of material that is too dense to remain suspended i.e. FDCA product. This material can be drawn off as it is formed, which allows for continuous operation. While the suspension reactor exemplified in FIG. 5 is one particularly favorable configuration, this does not exclude other reactor types and combinations from being utilized e.g. plug flow reactors (PFR), catalyst basket equipped stirred reactors known as "Carberry" reactors, fluidized bed reactors, batch or any combination of reactor types as would be known to a person having ordinary skill in the art.

In reactor 500, or other equivalent reactors, $CO_2$ can be continuously supplied to reactor 500 with a volumetric velocity such that a $CO_2$ saturated suspension fluid is maintained. This feed can be made through $CO_2$ feed inlet 505 or any other inlet configuration as schematically represented in FIG. 3 at 505. The effluent $CO_2$ stream, stream 507 in FIG. 3, can be utilized as a $CO_2$ recycle stream. In one configuration, the slurry within reactor 500 can be agitated and reactants remain suspended in the reactor for the duration of the residence time. Thus, FIG. 5 shows mixing impellers 510 that can be utilized for this purpose.

Under the conditions disclosed, the slurry and $CO_2$ in the reactor advantageously form particles of the mixture of reactants comprising a droplet or continuous phase of suspension fluid containing a reactant bead and at least one $CO_2$ bubble as schematically illustrated in the enlarged portion of FIG. 5. The $CO_2$ bubbles can advantageously be adhered or otherwise interacted with the solid reactants as shown, and this helps to produce excellent conditions for the desired reactions within the reactor.

Temperature within the reactor can preferably be maintained between 10 and 500° C., preferably between 100 and 300° C., and pressure can preferably be maintained between 3 and 15 bar.

In one configuration, a continuous draw from the reactor may be utilized through discharge 512 to draw off crude FDCA alkali metal salt product. Returning to FIG. 3, a finished reaction slurry exiting reactor 500 can be directed, for example through line 512, to a continuous separator shown at block 600. Separator 600 can be of any type common to industry for the separation of solid particles from fluids. Numerous options will be well known to a person having ordinary skill in the art. Separator 600 produces a separated suspension fluid which can be treated to remove any excess water produced during the carboxylation reaction and recycled back to the main blending area at mixer 400 by way of line 310.

The separated solids can be charged, via any suitable stream for example shown at 514 in FIG. 3, to a mixer unit as shown in block 700 for dissolution. The main function carried out in mixer unit 700 is to rapidly dissolve the reaction product that is formed. The resulting solution can then be charged to a precipitation reactor shown at block 800 for final product formation. The solution charged to reactor 800 can be reacted with a strong acid, shown at inlet stream 802, so that the FDCA alkali metal salt is protonated to FDCA and precipitated out of solution. The precipitated FDCA can be drawn off, as schematically illustrated at outlet 804, filtered from the solution and dried such that the typical product purity is ≥97% by mass. The alkali metal ions that are formed during the protonation reaction in reactor 800 can be charged to an ion exchange $CO_2$ absorption unit shown at block 900 by way of stream 806. Alkali metal ions can be reclaimed using any method that is common to industrial practices, including the use of hydroxyl ion producing ion exchange resins, as one non-limiting example. Regenerated alkali metal hydroxide(s) can be treated for purity and recycled to the process, for example via line 110 to oxidation reactor at block 200. A portion of the regenerated alkali metal hydroxide(s) can be diverted and treated with $CO_2$ to form an integral alkali metal carbonate promoter(s) and returned or recycled to the process via line 303.

Figure 7:
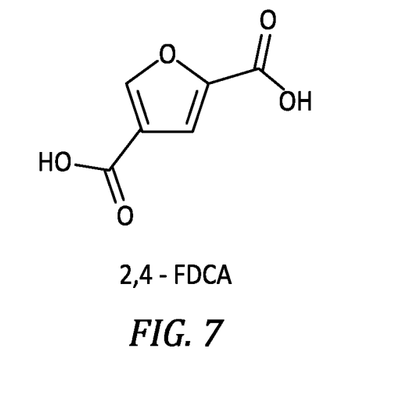
Figure 8:
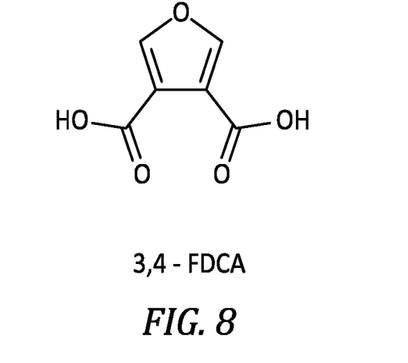
Figure 9:
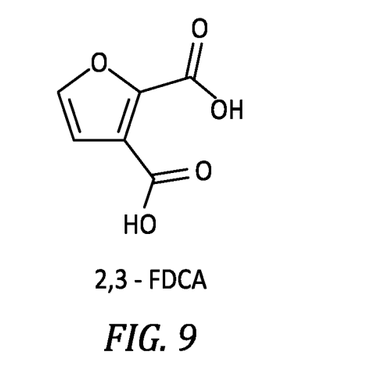

The presently disclosed embodiment details a process for the continuous production of 2,5-furandicarboxylic acid. Reagents and reaction conditions selectively target the fifth position of 2-furoate salt, where the hydrogen site is more acidic due to the adjoining carbon-oxygen bond. However, this process does not preclude production of associated isomers (2,4 FDCA, 2,3 FDCA, and 3,4 FDCA, see FIG. 7) using a comparable synthesis process. Further, any process is likely to produce a combination of these isomers in varying amounts. Thus, the process broadly refers to preparation of FDCA, with the specific disclosed embodiment being drawn to a process that produces a majority of 2,5-FDCA. It should be appreciated, however, that the present process could be modified by persons having ordinary skill in the art after consideration of this disclosure to produce different isomers in greater amount if desired, and these process as well are considered to fall within the broad scope of the present disclosure.

Returning to step 200 in FIG. 3, in the oxidation reaction, a furoic acid salt is formed from the reaction of furoic acid and alkali metal hydroxide (s). This furoic acid salt, in the presence of an alkali metal carbonate, can then be fed directly to the carboxylation reaction.

Figure 10:
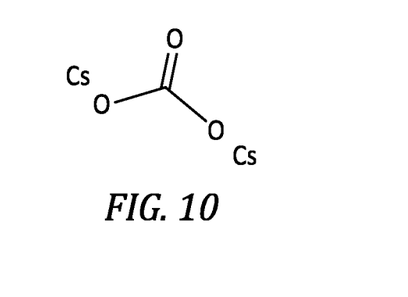
FIG. 10 is a molecular diagram of an alkali metal carbonate, in this case cesium carbonate, that is useful in the disclosed process.

The alkali metal carbonate can be any carbonate bearing mixtures or single elements of Li, Na, K, Rb, or Cs. FIG. 10 shows an example in the form of cesium carbonate.

Returning to the discussion of mixer 400 that is upstream of the carboxylation reactor 500 (FIG. 3), surfactants can be used in the disclosed process, for example to help mix the reactants and form the desired slurry to be fed to the carboxylation reactor. The surfactant can be chosen based on the needs of the reaction as well as the chemical makeups of the reagents involved in the reaction. Surfactants can be structurally defined as having a hydrophilic "head" with a lipophilic "tail". Surfactants vary widely beyond these two essential constructs. The lipophilic "tail" can be a saturated, or unsaturated hydrocarbon chain with a chain length of C3-C22 or it can contain ethers or other substitutions in the chain. The hydrophilic head can be any heteroatom with an associated dipole moment, either induced by covalent bonding or through ionic bonds. Due to the nature of the reagents used in this invention, a preference for anionic surfactants is noted. This is due to the ionic bond associated with the carboxylate functional group and alkali metal atom in the furan ring. The use of anionic surfactants is particularly useful in the disclosed process, as the polar surfactant is attracted to the carboxylate molecules but does not react with said carboxylate. Particularly suitable surfactants include but are not limited to cesium stearate, sodium stearate, potassium stearate and other stearic acid derived surfactants.

The role of surfactants in the process can be significant. Surfactants act as an agent to lower the surface tension associated with the immiscible particles and the fluid which allows for the particle's free movement through the fluid. They also act as a means to prevent agglomeration through the formation of macromolecules known as micelles. Micelles form a double layer, or two surfaces with like charges, that act to repel each other and prevent agglomeration of the particles, and this leads to better mixing in mixer 400 and reactivity in reactor 500.

Figure 11:
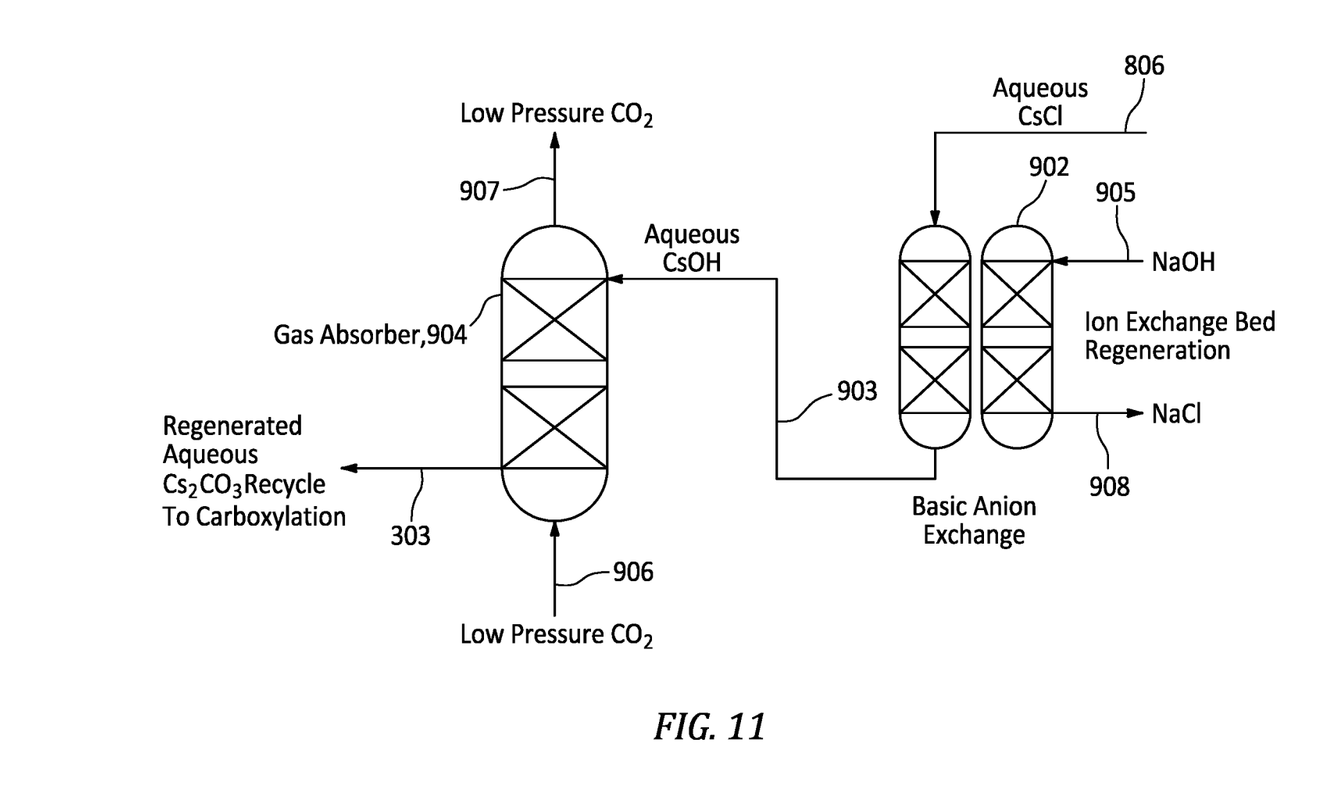
FIG. 11 schematically illustrates another portion of the integrated process wherein alkali metal and carbonate regeneration is conducted.

Due to the large mass and high cost of the alkali metal carbonate used as a promoter in the carboxylation reaction, an efficient means for regeneration of that promoter is an important component of a successfully integrated manufacturing process. FIG. 11 illustrates a process for this regeneration. Acidification and precipitation of FDCA from an aqueous solution of FDCA alkali metal salt using HCl will result in an aqueous solution containing alkali metal chloride (s).

The alkali metal associated with the chlorine ion of these alkali metal chlorides can be recovered by first passing the filtrate solution in stream 806 from precipitation reactor 800 through ion exchange such as a strongly basic anion exchange resin 902 to convert the alkali metal chloride to an alkali metal hydroxide. Shown at line 903. Removal of chloride anions and replacement with hydroxyl anions is routinely practiced as part of conventional water demineralization treatment, and is shown in this example as entry of hydroxide such as sodium hydroxide in stream 905 and exit of a stream 908 of chloride, in this example sodium chloride.

The resulting aqueous alkali metal hydroxide solution in line 903 can then be reused in the oxidation sequence of the process (line 110, FIG. 3) or can be further treated to regenerate to the alkali metal carbonate promoter(s).

Further treatment to obtain alkali metal carbonate promoter can be accomplished by feeding stream 903 to gas absorber 904 where the aqueous alkali metal hydroxide is contacted with a cross flow of low pressure $CO_2$ as shown at low pressure $CO_2$ inlet 906 and outlet 907. The resulting carbonate, such as $Cs_2CO_3$, is regenerated in a 2-step reaction of the alkali metal hydroxide(s) with carbon dioxide which can be recycled to the carboxylation reactor 500.

It should be appreciated that carbon dioxide reacts with water to form carbonic acid, which quickly reacts with the alkali metal hydroxide(s) to form carbonate. This reaction sequence, while forming one path for regeneration of the alkali metal carbonate, does not limit the disclosure to only the alkali metal path shown, and also not only to the illustrated alkali metal cesium, but can apply to any alkali metal hydroxide and regeneration through other mechanisms.

Example 1

An aqueous solution was formed reacting 9.6 g 2-furoic acid and 48.5 g cesium carbonate. The molar ratio of the reactants was 1 mol furoic acid to 1.75 mol cesium carbonate (Block 200 FIG. 3). The aqueous solution was then dried to a water content of 3.5 weight percent as measured by KF titration (Block 300 FIG. 3).

The cesium furoate/cesium carbonate mixture was charged to a 450 mL glass Parr reactor liner and admixed with 0.5 g cesium stearate (Block 400 FIG. 3). This represents a 0.8 weight percent of the anionic surfactant to the cesium furoate/cesium carbonate mixture. The liner and solids material were then charged to a Parr systems Hastelloy C pressure reactor, the reactor head was affixed with dual pitched blade impellers, spaced sufficiently apart to provide mixing in the reactor (Block 500 FIG. 3).

A hydrocarbon suspension fluid, such as in this case, Iso Par V produced by ExxonMobil, was then pumped directly to the Parr reactor, providing a 7:1 mass ratio of suspension fluid to solids (cesium furoate/cesium carbonate/cesium stearate). The reaction was then initiated at 260° C., at 8 bar pressure, and 60 mL/min $CO_2$ flow rate for a period of 5 hours. Upon completion, the reactor was evacuated of its contents.

The solids were recovered by vacuum filtration using a Buchner funnel and Whatman qualitative filtering paper (Block 600 FIG. 3). The filtered solids were dissolved in distilled water and passed through a 250 mL separatory funnel to separate the suspension fluid from the aqueous solution (Block 700).

The filtrate recovered from the separatory funnel was then used to create samples for HPLC UV spectra analysis, using a Perkin Elmer Series 200 HPLC column with a Shodex SH1011 analytical column. According to analysis of HPLC UV spectra, a cesium furoate conversion of 81.5% and a 2,5-furan dicarboxylate selectivity of 95% was achieved, this produced a 78.0% yield. These results are listed in Table 1 under the Run ID "A". Conversion of the 40 mmol of cesium furoate as well as selectivity and yield of the 2,5-furan dicarboxylate was calculated using equations 1-3:

$$X_{furoate} = \frac{n_{furoate\,input} - n_{furoate\,output}}{n_{furoate\,input}} \quad (1)$$

$$S_{dicarboxylate} = \frac{n_{dicarboxylate}}{X_{furoate} * n_{furoate\,input}} \quad (2)$$

$$Y_{dicarboxylate} = X_{furoate} * S_{dicarboxylate} * 100 \quad (3)$$

Where X is conversion, S is selectivity, Y is yield, and n is mole of the labeled substance.

Example 2

This reaction follows the procedure of Example 1 with one notable change. In this example, 0.11 g of sodium stearate is substituted for cesium stearate, which represents 0.4 weight percent of the furoate salt mass. The reaction was then initiated at 260° C., at 8 bar pressure, and 60 mL/min $CO_2$ flow rate for a period of 5 hours. Upon completion, the reactor was evacuated of its contents.

HPLC UV spectra analysis determined that an 82.5% conversion of the furoate salt, and a 92.1% selectivity of the furan dicarboxylate salt were achieved resulting in a 76% yield. These results are listed in Table 1 as Run ID "B".

Two additional runs were conducted with adjustments to surfactant ratios as Runs "C" and "D".

Example 3

In this example cesium furoate is prepared by reacting 9.65 g of 2-furoic acid with 28.94 g cesium carbonate. Cesium stearate was again used in this reaction, with a deviation in the loading of the alkali metal carbonate promoter. In this example the cesium carbonate was not prepared in excess with the aqueous cesium furoate solution, but rather was loaded into the reactor as a separate entity (Block 400 FIG. 3). The cesium carbonate was dried separately from the cesium furoate.

32.49 g dried cesium furoate and 18.82 g of cesium carbonate were charged to a 450 mL glass Parr reactor liner, resulting in a mass ratio of 1:1.7 cesium furoate to cesium carbonate, coupled with 0.1 g of cesium stearate. The Iso Par V suspension fluid was charged to the system at 3:1 mass ratio of suspending fluid to solids. The reaction was then initiated at 260° C., at 8 bar pressure, and 60 mL/min $CO_2$ flow rate for a period of 5 hours. Upon completion, the reactor was evacuated of its contents.

HPLC UV spectra revealed a cesium furoate conversion of 87% with a furan dicarboxylate selectivity of 81%, giving a furan dicarboxylate yield of ~70%. These results are listed in Table 1 as Run ID "E".

Example 4

9.6 g of 2-furoic acid and 35.05 g cesium carbonate were admixed in a 250 mL round bottom flask, creating a 1 mol to 1.25 mol ratio of 2-furoic acid to cesium carbonate. The mixed solids were dissolved in 13 g of distilled water and dried under 29 in Hg vacuum at 230° C., until the moisture content of the dried material was 3.24 weight percent. The dried material was ground to a fine powder and charged to the same reactor setup described in Example 1 with a 3:1 mass ratio of suspension fluid to solids. The reaction was then initiated at 260° C., at 8 bar pressure, and 60 mL/min $CO_2$ flow rate for a period of 3 hours. Upon completion, the reactor was evacuated of its contents. This produced a furoate conversion of 65.4%, and an FDCA selectivity of 99.5%, giving a FDCA yield of 65%, Run ID "F".

Example 5

A 1 mol to 1 mol solution of cesium carbonate to 2-furoic acid was dried to a moisture content of 2.493 weight percent. Of the dried material, 43.81 g (0.1 mol cesium furoate), 0.18 g cesium stearate surfactant, and 135 g Isopar V (ExxonMobil) were charged to the 450 cc Hastelloy C glass lined Parr reactor. The reaction was then initiated at 260° C., at 8 bar pressure, and 60 mL/min $CO_2$ flow rate for a period of 5 hours. Upon completion, the reactor was evacuated of its contents. A yield of 69.94% was achieved, Table 1, Run ID "G".

Example 6: No Surfactant Present During the Carboxylation Reaction

An aqueous solution was produced from 4.8 g 2-furoic acid and 25.27 g cesium carbonate on a 1:1.75 2-furoic acid to cesium carbonate molar ratio. The material was then dried to a moisture content of approximately 5 weight percent. The solids mixture was then charged to a 450 cc glass Parr reactor liner with Iso Par V suspending fluid such that the mass ratio of suspending fluid to solids was 7:1, in the absence of a surfactant. The liner and its contents were charged to the 450 cc Hastelloy C Parr reactor and sealed. The reaction was then initiated at 260° C., at 8 bar pressure, and 60 mL/min $CO_2$ flow rate for a period of 5 hours. Upon completion, the reactor was evacuated of its contents.

Post reaction a large immobile mass of product had formed. From the glass liner the Iso Par V was decanted with the solids agglomerated to the sidewalls and bottom of the liner. The solids were dissolved in room temperature distilled water, upon dissolution insoluble particles were observed. The solution was passed through a 250 mL separatory funnel to separate Iso Par V suspension fluid from the aqueous solution. From examination of the HPLC UV spectra it was determined that this reaction produced a 52% yield from a 72% furoate conversion and 73% FDCA selectivity, Run ID "H".

TABLE 1

Run Results for Suspension Carboxylation
(260° C., 8 bar pressure)

| Run Id | Reaction Time (Hours) | Conversion of Furoic acid | Selectivity of FDCA | Yield of FDCA |
| --- | --- | --- | --- | --- |
| A | 5 | 81.5% | 95.7% | 78.0% |
| B | 5 | 82.5% | 92.1% | 76.0% |
| C | 5 | 81.95% | 85.96% | 70.5% |
| D | 5 | 81.31% | 86.65% | 70.5% |
| E | 5 | 86.35% | 80.98% | 69.9% |
| F | 3 | 65.4% | 99.5% | 65.1% |
| G | 5 | 70.58% | 98.33% | 69.4% |
| H | 5 | 71.5% | 73.6% | 52.6% |

The present disclosure provides details on one or more embodiments or configurations of a process for making 2,5-FDCA and its isomers. It should also be noted that while various details of the disclosed have been shown to be of importance in producing intended results, other configurations are possible and will be apparent to a person having ordinary skill in the art, upon consideration of this disclosure. The disclosed configurations can be utilized individually, or in combination with each other, and any such combination of these configurations is considered to be within the scope of this disclosure. Further, the variations in specific aspects of the disclosure as referred to above would be well within the scope of the present disclosure.

One or more embodiments have been described. Nevertheless, it will be understood that various modifications may be made. For example, different combinations of reactants could be utilized, or a different specific type of reactor could be utilized for one or more of the steps of the process. These modifications can influence details of particular implementations, but are otherwise within the scope of this disclosure. Accordingly, other embodiments are within the scope of the following claims.

We claim:

1. A process for carboxylation of a furoate slurry to produce FDCA, comprising the steps of:
   feeding a slurry containing a suspension fluid, furoate, a surfactant and an alkali metal carbonate to a carboxylation reactor; and
   feeding a flow of $CO_2$ to the carboxylation reactor at flow conditions sufficient to suspend the slurry in the reactor and react the furoate with $CO_2$ to form FDCA,
   wherein the suspension fluid is present in the slurry at a mass ratio of suspension fluid to solids in the slurry of between 7:1 and 1:1; and
   wherein the slurry contains surfactant and furoate at a furoate to surfactant mass ratio of between 4:1 and 628:1.

2. The process of claim 1, wherein the FDCA comprises a majority fraction of 2,5-FDCA.

3. The process of claim 1, wherein the suspension fluid demonstrates characteristics sufficient to maintain a suspension of reactant particles, readily absorbs $CO_2$, is thermally stable and non-flammable.

4. The process of claim 1, wherein the suspension fluid is selected from the group consisting of paraffinic solution, fatty acid solution, and combinations thereof.

5. The process of claim 1, wherein a temperature in the reactor is between 10 and 500° C.

6. The process of claim 5, wherein the temperature in the reactor is between 100 and 300° C.

7. The process of claim 1, wherein pressure in the reactor is between 3 and 15 bar.

8. The process of claim 1, wherein the alkali metal carbonate is a promoter and can contain an alkali metal that is the same or different from the surfactant and the furoate.

9. The process of claim 1, wherein the slurry and the $CO_2$ in the reactor form particles of mixture comprising a droplet of suspension fluid containing a reactant bead and at least one $CO_2$ bubble.

10. The process of claim 1, wherein a finished reaction slurry is removed from the reactor, and further comprising feeding the finished reaction slurry to a solid/fluid separator to produce separated solids, feeding the separated solids to a dissolver/mixer unit to dissolve the solids to produce a dissolved product, and feeding the dissolved product to a precipitation reactor to precipitate and separate the desired 2,5 FDCA.

11. The process of claim 1, wherein the slurry is prepared by mixing a dried furoate with the surfactant and the alkali metal carbonate with the suspension fluid in a mixer.

12. The process of claim 11, wherein the alkali metal carbonate is regenerated from an alkali metal chloride by ion exchange into an alkali metal hydroxide and then gas absorption of the alkali metal hydroxide with $CO_2$ to produce the alkali metal carbonate.

13. The process of claim 1, wherein the furoate is prepared by oxidizing furfural in the presence of an alkali metal hydroxide.

14. The process of claim 13, wherein the furfural is prepared by reactive distillation of a C5 sugar source in the presence of an acid catalyst and polymerization inhibitor.

15. An integrated process for preparation of FDCA, comprising the steps of:

feeding furfural and alkali metal hydroxide to an oxidation reactor to produce furoate;

feeding the furoate to a drier to produce a dried furoate;

feeding the dried furoate, an alkali metal carbonate, a surfactant and a suspension fluid to a mixer to form a slurry;

feeding the slurry to a carboxylation reactor for contacting with a stream of $CO_2$ so as to produce a finished product containing FDCA;

feeding the finished product to a solid/fluid separator to generate a separated fluid and a solid finished product;

feeding the solid finished product to a dissolver/mixer to form a dissolved finished product, and feeding the dissolved finished product to a precipitation reactor in the presence of an acid to obtain a final FDCA product and an alkali chloride;

recycling the separated fluid from the solid/fluid separator to the mixer as recycle suspension fluid;

feeding the alkali chloride from the precipitation reactor to an ion exchange reactor to produce a recycled alkali metal hydroxide as recycle feed to the oxidation reactor, and feeding at least a portion of the recycled alkali metal hydroxide to contact a $CO_2$ stream in a gas absorber to produce a regenerated alkali metal carbonate; and recycling the regenerated alkali metal carbonate to the mixer.

16. The process of claim 15, wherein the FDCA comprises a majority fraction of 2,5-FDCA.

17. The process of claim 15, further comprising feeding a C5 sugar bearing source to a catalytic and reactive distillation process to produce the furfural.

* * * * *